(12) United States Patent
Nakano et al.

(10) Patent No.: US 11,712,065 B2
(45) Date of Patent: Aug. 1, 2023

(54) FLAVOR INHALER AND ATOMIZING UNIT

(71) Applicant: JAPAN TOBACCO INC., Tokyo (JP)

(72) Inventors: Takuma Nakano, Tokyo (JP);
Hirofumi Matsumoto, Tokyo (JP);
Manabu Yamada, Tokyo (JP)

(73) Assignee: JAPAN TOBACCO INC., Tokyo (JP)

( * ) Notice: Subject to any disclaimer, the term of this patent is extended or adjusted under 35 U.S.C. 154(b) by 1156 days.

(21) Appl. No.: 16/373,048

(22) Filed: Apr. 2, 2019

(65) Prior Publication Data

US 2019/0223512 A1    Jul. 25, 2019

Related U.S. Application Data

(63) Continuation of application No. PCT/JP2016/079615, filed on Oct. 5, 2016.

(51) Int. Cl.
| | |
|---|---|
| *A24F 40/51* | (2020.01) |
| *H05B 3/10* | (2006.01) |
| *H05B 1/02* | (2006.01) |
| *A61M 15/06* | (2006.01) |
| *A24F 40/46* | (2020.01) |
| *A61M 11/04* | (2006.01) |
| *C23C 16/448* | (2006.01) |
| *A24F 40/10* | (2020.01) |
| *A24F 40/50* | (2020.01) |

(52) U.S. Cl.
CPC .............. *A24F 40/51* (2020.01); *A24F 40/46* (2020.01); *A61M 11/042* (2014.02); *A61M 15/06* (2013.01); *H05B 1/0297* (2013.01); *H05B 3/10* (2013.01); *A24F 40/10* (2020.01); *A24F 40/50* (2020.01); *C23C 16/4481* (2013.01)

(58) Field of Classification Search
CPC .............. A61M 15/06; A61M 15/0003; A61M 11/042; A24F 40/51; A24F 40/30; A24F 40/40; A24F 40/48; A24F 40/10
See application file for complete search history.

(56) References Cited

U.S. PATENT DOCUMENTS

| | | | |
|---|---|---|---|
| 9,067,029 B2* | 6/2015 | Yamada | ................. A61M 15/00 |
| 10,368,580 B2* | 8/2019 | Rostami | ................... A24F 40/44 |
| 10,499,688 B2* | 12/2019 | Dickens | ............... H05B 1/0244 |
| 2012/0048266 A1* | 3/2012 | Alelov | ................. A61M 15/008 |
| | | | 128/203.14 |

(Continued)

FOREIGN PATENT DOCUMENTS

| | | |
|---|---|---|
| EP | 0845220 A1 | 6/1998 |
| EP | 2022350 A1 | 2/2009 |

(Continued)

OTHER PUBLICATIONS

Japanese Office Action for Japanese Application No. 2018-543527, dated Apr. 1, 2020, with machine English translation.

(Continued)

*Primary Examiner* — Marcus E Harcum
(74) *Attorney, Agent, or Firm* — Birch, Stewart, Kolasch & Birch, LLP

(57) ABSTRACT

A flavor inhaler includes a heating element that atomizes an aerosol source and a supply member that has a discharge port for supplying the aerosol source to the heating element. The heating element has a porous structure, and is disposed apart from the discharge port.

14 Claims, 12 Drawing Sheets

(56) References Cited

U.S. PATENT DOCUMENTS

| | | | |
|---|---|---|---|
| 2013/0081623 A1 | 4/2013 | Buchberger | |
| 2014/0109905 A1 | 4/2014 | Yamada et al. | |
| 2014/0238422 A1 | 8/2014 | Plunkett et al. | |
| 2014/0261488 A1* | 9/2014 | Tucker | A24F 40/50 131/328 |
| 2014/0261492 A1* | 9/2014 | Kane | A24F 40/485 131/328 |
| 2015/0114409 A1 | 4/2015 | Brammer et al. | |
| 2015/0117841 A1 | 4/2015 | Brammer et al. | |
| 2015/0117842 A1 | 4/2015 | Brammer et al. | |
| 2016/0262457 A1* | 9/2016 | Borkovec | A61M 15/002 |
| 2017/0042242 A1 | 2/2017 | Hon | |
| 2017/0071261 A1* | 3/2017 | Tucker | A24F 40/51 |
| 2017/0119058 A1* | 5/2017 | Cameron | A24B 15/167 |
| 2017/0157341 A1* | 6/2017 | Pandya | A61M 15/009 |
| 2017/0238605 A1 | 8/2017 | Matsumoto et al. | |
| 2017/0251721 A1* | 9/2017 | Rostami | A61M 15/0003 |
| 2017/0258138 A1* | 9/2017 | Rostami | A24F 40/30 |
| 2017/0303586 A1* | 10/2017 | Sur | H05B 3/145 |
| 2018/0027875 A1* | 2/2018 | Rostami | H05B 3/42 |
| 2018/0042306 A1* | 2/2018 | Atkins | H05B 1/0297 |
| 2018/0263286 A1* | 9/2018 | Reevell | B01F 23/2133 |
| 2018/0263296 A1* | 9/2018 | Sebastian | A24F 40/50 |
| 2018/0289069 A1* | 10/2018 | Reevell | H02J 7/34 |
| 2018/0325176 A1* | 11/2018 | Burseg | A24F 40/50 |
| 2019/0001077 A1* | 1/2019 | Xu | A24F 40/44 |
| 2019/0124982 A1* | 5/2019 | Atkins | A24F 40/30 |
| 2019/0183177 A1* | 6/2019 | Hubbard | A61M 11/042 |
| 2019/0289909 A1* | 9/2019 | Hejazi | A24B 15/167 |
| 2020/0037667 A1* | 2/2020 | Woodcock | G08B 5/40 |
| 2020/0068949 A1* | 3/2020 | Rasmussen | H05B 1/0297 |
| 2020/0113232 A1* | 4/2020 | Bless | A24F 40/30 |
| 2020/0390149 A1* | 12/2020 | Hepworth | A61M 15/06 |

FOREIGN PATENT DOCUMENTS

| | | |
|---|---|---|
| EP | 2 719 416 A1 | 4/2014 |
| JP | 3325028 B2 | 9/2002 |
| JP | 2009-537120 A | 10/2009 |
| JP | 2014-191932 A | 10/2014 |
| TW | 360502 B | 6/1999 |
| TW | 201616989 A | 5/2016 |
| TW | I630879 B | 8/2018 |
| WO | WO 2013/027249 A1 | 2/2013 |
| WO | WO 2015/114325 A1 | 8/2015 |

OTHER PUBLICATIONS

Japanese Office Action for Japanese Application No. 2018-543527, dated Oct. 28, 2020, with English translation.
Korean Office Action for Korean Application No. 10-2019-7012521, dated Oct. 14, 2020, with English translation.
Taiwanese Office Action, dated May 5, 2020, for Taiwanese Application No. 106129325, along with an English translation.
Taiwanese Office Action and Search Report for Taiwanese Application No. 106129325, dated Jun. 25, 2019, with English translation.
International Search Report for International Application No. PCT/JP2016/079615, dated Dec. 27, 2016, with English translation.
Extended European Search Report dated Apr. 30, 2020, for the corresponding European patent application No. 16918287.0.

* cited by examiner

FLAVOR INHALER AND ATOMIZING UNIT

CROSS REFERENCE TO RELATED APPLICATIONS

This application is a Continuation of PCT International Application No. PCT/JP2016/079615, filed on Oct. 5, 2016, which is hereby expressly incorporated by reference into the present application.

TECHNICAL FIELD

The present invention relates to a flavor inhaler and an atomizing unit for inhaling flavor without combustion.

BACKGROUND ART

Conventionally, a flavor inhaler for inhaling flavor without combustion is known. The flavor inhaler has a heating element that atomizes an aerosol source without combustion, and a supply member that supplies an aerosol source to the heating element (for example, PTL 1 to 3).

CITATION LIST

Patent Literature

PTL 1: Specification of U.S. Pat. No. 2015/0117841
PTL 2: Specification of U.S. Pat. No. 2015/0117842
PTL 3: Specification of U.S. Pat. No. 2015/0114409

SUMMARY OF INVENTION

A first feature is a flavor inhaler including: a heating element that atomizes an aerosol source; and a supply member that has a discharge port for supplying the aerosol source to the heating element, wherein the heating element has a porous structure, and is disposed apart from the discharge port.

According to a second feature, in the first feature, the heating element is a heating resistor composing the porous structure.

According to a third feature, in the first feature or the second feature, the flavor inhaler includes a control unit that controls atomization of the aerosol source by the heating element, wherein in a case in which a supply start condition is satisfied, supply of the aerosol source is started, and in case that a heating start condition is satisfied after the supply start condition is satisfied, the control unit starts heating of the heating element.

According to a fourth feature, in the third feature, in case that a supply end condition is satisfied, supply of the aerosol source is ended, and in case that a heating end condition is satisfied after the supply end condition is satisfied, the control unit ends heating of the heating element.

According to a fifth feature, in the third feature or the fourth feature, the heating start condition is that first predetermined time elapses after the supply start condition is satisfied.

According to a sixth feature, in the third feature or the fourth feature, the flavor inhaler includes an inhalation sensor that detects puff operation of a user, wherein the heating start condition is determined on the basis of a value output from the inhalation sensor.

According to a seventh feature, in the third feature or the fourth feature, the flavor inhaler includes a detection sensor that detects first predetermined manipulation of a user, wherein the heating start condition is to detect the first predetermined manipulation.

According to an eighth feature, in any of the fourth feature, and the fifth feature to the seventh feature citing the fourth feature, the heating end condition is that second predetermined time elapses after the supply end condition is satisfied.

According to a ninth feature, in any of the fourth feature, and the fifth feature to the seventh feature citing the fourth feature, the flavor inhaler includes an inhalation sensor that detects puff operation of a user, wherein the heating end condition is determined on the basis of a value output from the inhalation sensor.

According to a tenth feature, in any of the fourth feature, and the fifth feature to the seventh feature citing the fourth feature, the flavor inhaler includes a detection sensor that detects second predetermined manipulation of a user, wherein the heating start condition is to detect the second predetermined manipulation.

According to an eleventh feature, in any of the fourth feature, and the fifth feature to the tenth feature citing the fourth feature, in case that time from when the supply end condition is satisfied until when the heating end condition is satisfied is shorter than predetermined time in n (n is an integer of one or more)-th puff operation, when a more relaxed condition than the heating start condition is satisfied in (n+1)-th puff operation, the control unit starts heating of the heating element.

According to a twelfth feature, in any of the fourth feature, and the fifth feature to the eleventh feature citing the fourth feature, in case that time from when the supply end condition is satisfied until when the heating end condition is satisfied is shorter than predetermined time in n (n is an integer of one or more)-th puff operation, the control unit controls atomization of the aerosol source by the heating element such that electric power larger than electric power supplied to the heating element in the n-th puff operation is supplied to the heating element in (n+1)-th puff operation.

According to a thirteenth feature, in the eighth feature, in case that end of the puff operation of the user is detected before the second predetermined time elapses after the supply end condition is satisfied, the control unit ends heating of the heating element before the second predetermined time elapses.

According to a fourteenth feature, in the thirteenth feature, in case that heating of the heating element is ended before the second predetermined time elapses in n (n is an integer of one or more)-th puff operation, when a more relaxed condition than the heating start condition is satisfied in (n+1)-th puff operation, the control unit starts heating of the heating element.

According to a fifteenth feature, in the thirteenth feature or the fourteenth feature, in case that heating of the heating element is ended before the second predetermined time elapses in n (n is an integer of one or more)-th puff operation, the control unit controls atomization of the aerosol source by the heating element such that electric power larger than electric power supplied to the heating element in the n-th puff operation is supplied to the heating element in (n+1)-th puff operation.

According to a sixteenth feature, in the first feature or the second feature, the flavor inhaler includes a control unit that controls atomization of the aerosol source by the heating element, wherein in case that a supply start condition is satisfied, supply of the aerosol source is started, the control unit controls atomization of the aerosol source such that a temperature of the heating element becomes less than a boiling point of the aerosol source until the supply start condition is satisfied, and the control unit controls atomization of the aerosol source such that a temperature of the heating element becomes not less than the boiling point of the aerosol source after the supply start condition is satisfied.

According to a seventeenth feature, in the any of the first feature to the sixteenth feature, an absorbing member that absorbs aerosol which flocculates on a wall surface of a flow passage is provided on the flow passage for the aerosol generated by atomization of the aerosol source.

According to an eighteenth feature, in any of the fourth feature, and the fifth feature to the seventeenth feature citing the fourth feature, the control unit controls atomization of the aerosol source by the heating element such that electric power larger than electric power supplied before the supply end condition is satisfied is supplied to the heating element from when the supply end condition is satisfied until when the heating end condition is satisfied.

A nineteenth feature is an atomizing unit including: a heating element that atomizes an aerosol source; and a supply member that has a discharge port for supplying the aerosol source to the heating element, wherein the heating element has a porous structure, and is disposed apart from the discharge port.

DESCRIPTION OF EMBODIMENTS

Figure 1:
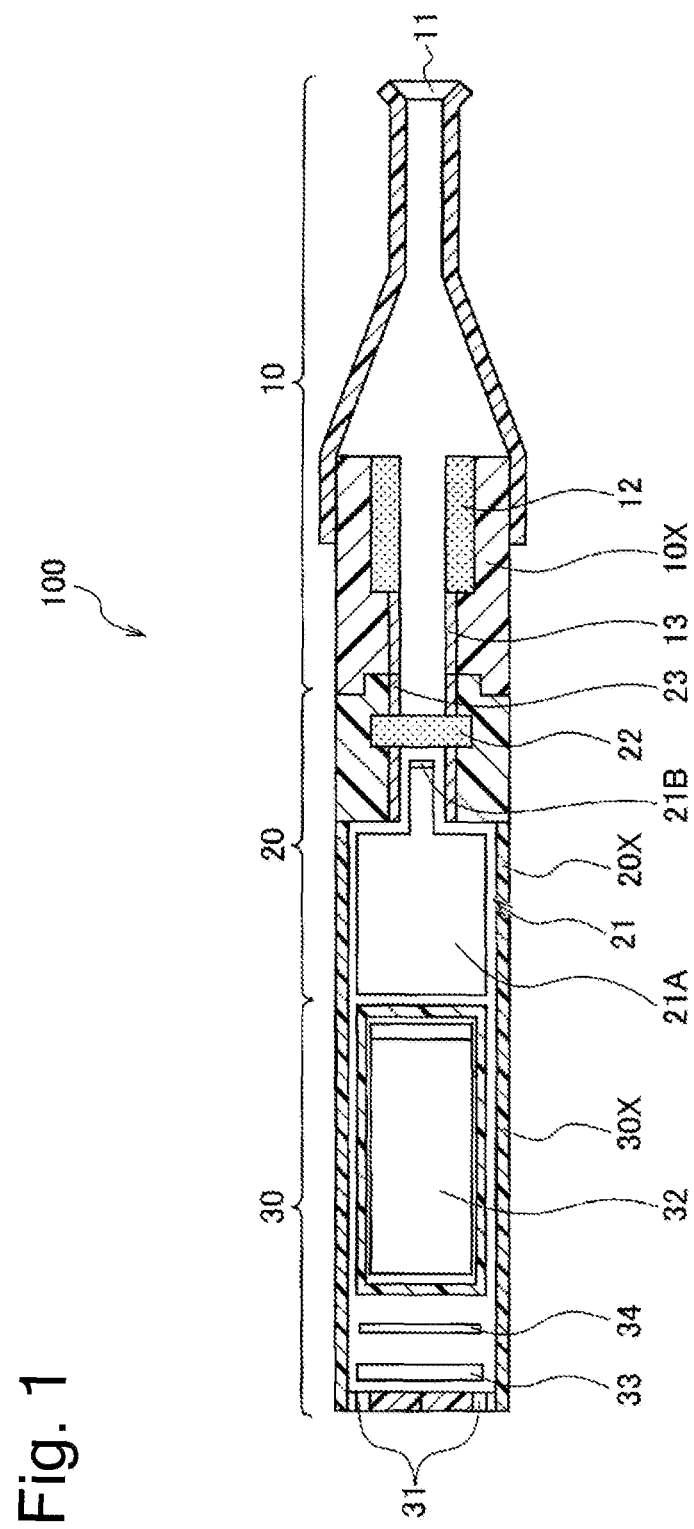
FIG. 1 is a diagram illustrating a flavor inhaler 100 according to an embodiment.

Hereinafter, an embodiment will be described. In the following illustration of the drawings, the same or similar portions are denoted by the same or similar reference numerals. However, the drawings are schematically illustrated, and it should be noted that the ratios of respective dimensions and the like are sometimes different from actual ones.

Accordingly, specific dimensions and the like should be determined by taking into consideration the following description. Of course, portions whose dimensional relations and ratios are different between drawings are sometimes included.

SUMMARY OF DISCLOSURE

In the flavor inhaler described in BACKGROUND ART, a heating element itself does not have a function of holding an aerosol source, and therefore a member for holding an aerosol source to be supplied to the vicinity of the heating element (for example, a net) needs to be provided separately in order to efficiently atomize the aerosol source.

The flavor inhaler according to SUMMARY OF DISCLOSURE includes: a heating element that atomizes an aerosol source; and a supply member that has a discharge port for supplying the aerosol source to the heating element, wherein the heating element has a porous structure, and is disposed apart from the discharge port. According to such a configuration, the heating element itself has the porous structure, and therefore the heating element can hold the aerosol source, a member for holding the aerosol source does not need to be provided separately, and the aerosol source can be efficiently atomized. Furthermore, the heating element is disposed apart from the discharge port, and therefore heat transfer from the aerosol source on the heating element side to the aerosol source on the supply member side is suppressed in a state in which the aerosol source is not supplied from the supply member to the heating element.

Embodiments (Flavor Inhaler)

Hereinafter, a flavor inhaler according to an embodiment will be described. FIG. 1 is a diagram illustrating a flavor inhaler 100 according to the embodiment.

As illustrated in FIG. 1, the flavor inhaler 100 has a mouthpiece unit 10, an atomizing unit 20, and an electric unit 30. The mouthpiece unit 10 may be detachably attached to the atomizing unit 20. The atomizing unit 20 may be detachably attached to the electric unit 30.

The mouthpiece unit 10 has a case 10X, an outlet 11, an absorbing component 12, and a flow passage member 13. The case 10X houses the outlet 11, the absorbing component 12, and the flow passage member 13.

The outlet 11 is an outlet (opening) of an air flow passage that communicates from an inlet 31 described below to the outlet 11. The outlet 11 is provided in a root end (mouthpiece end) of the flavor inhaler 100.

The absorbing component 12 absorbs aerosol that flocculates on a wall surface of a flow passage (a part of the air flow passage) for aerosol generated by the atomizing unit 20. The absorbing component 12 is provided on an inner wall surface of the flow passage member 13. The absorbing component 12 only needs to be a member having a function of absorbing flocculated aerosol, and may be, for example, a porous member such as a sponge, a resin web, a glass fiber, or the like.

The flow passage member 13 is a member that forms a part of the air flow passage (herein, a flow passage for aerosol). The flow passage member 13 has a cylindrical shape.

The atomizing unit 20 has a case 20X, a supply member 21, a heating element 22, and a flow passage member 23. The case 20X houses the supply member 21, the heating element 22, and the flow passage member 23.

The supply member 21 supplies an aerosol source to the heating element 22. More specifically, the supply member 21 has a storage part 21A that stores the aerosol source, and a discharge port 21B that supplies the aerosol source to the heating element 22. The discharge port 21B may include discharging means for supplying droplets of the aerosol source to the heating element 22 by control of a control circuit 34 described below. A droplet supply method is similar to a method used in an ink jet printer, and may be an ultrasonic method, a piezoelectric method, or a thermal method. The aerosol source is liquid such as glycerin and propylene glycol. The aerosol source, the aerosol source may contain a flavor component (for example, a nicotine component or the like). Alternatively, the aerosol source may not contain the flavor component.

The heating element 22 atomizes the aerosol source. The heating element 22 has a porous structure, and is disposed apart from the discharge port 21B.

The heating element 22 has a function of temporarily holding the aerosol source. A member composing the heating element 22 is not specially limited, as long as the member has a function of atomizing an aerosol source by electric heating. The heating element 22 may be a heating resistor having a porous structure. As such a heating resistor, a porous metal body containing for example, nickel, nichrome, of stainless steel (SUS) can be used. As the heating resistor, as long as the heating resistor is a conductive material capable of generating heat by electric heating, ceramics such as silicon carbide (SiC) may be used.

In the embodiment, the heating element 22 has a three-dimensional network structure. The three-dimensional network structure includes voids, and has a structure in which at least some voids communicate, that is, has an open-cell structure. The heating element 22 may have a function of sucking up the aerosol source by a capillary phenomenon. An example of the heating element 22 having the open-cell structure is CELMET (trade name) manufactured by Sumitomo Electric Industries, Ltd. can be cited. CELMET (trade name) is a porous metal body containing nickel (Ni), or a porous metal body containing an alloy of nickel and chromium (Cr).

The flow passage member 23 is a member that forms a part of the air flow passage. The flow passage member 23 has a cylindrical shape, and is continued to the above flow passage member 13. The above absorbing component 12 may be provided on both inner wall surfaces of the flow passage member 13 and the flow passage member 23. The absorbing component 12 may be provided on the inner wall surface of only both the flow passage member 23.

The electric unit 30 has a case 30X, the inlet 31, a battery 32, an inhalation sensor 33, and the control circuit 34. The case 30X houses the inlet 31, the battery 32, the inhalation sensor 33, and the control circuit 34.

The inlet 31 is an inlet (opening) of the air flow passage that communicates from the inlet 31 to the outlet 11. The inlet 31 may be provided in a tip (non-mouthpiece end) of the flavor inhaler 100. However, the position of the inlet 31 is not particularly limited, and the inlet may be provided in a side surface of the flavor inhaler 100. The inlet 31 may be provided in the atomizing unit 20.

The battery 32 stores electric power necessary for driving the flavor inhaler 100. The battery 32 may be a rechargeable secondary battery. The battery 32 is, for example, a lithium-ion battery.

The inhalation sensor 33 outputs a value (for example, a voltage value or a current value) changed by an air flow in the air flow passage. For example, the inhalation sensor 33 has a capacitor, and may output a value indicating electric power capacity of the capacitor that is changed by the air flow in the air flow passage. The inhalation sensor 33 may output a flow velocity value obtained by conversion of a value changed by the air flow in the air flow passage.

The control circuit 34 is composed of a CPU, a memory and the like, and controls operation of the flavor inhaler 100. Details of the control circuit 34 will be described below.

(Control Circuit)

Figure 2:
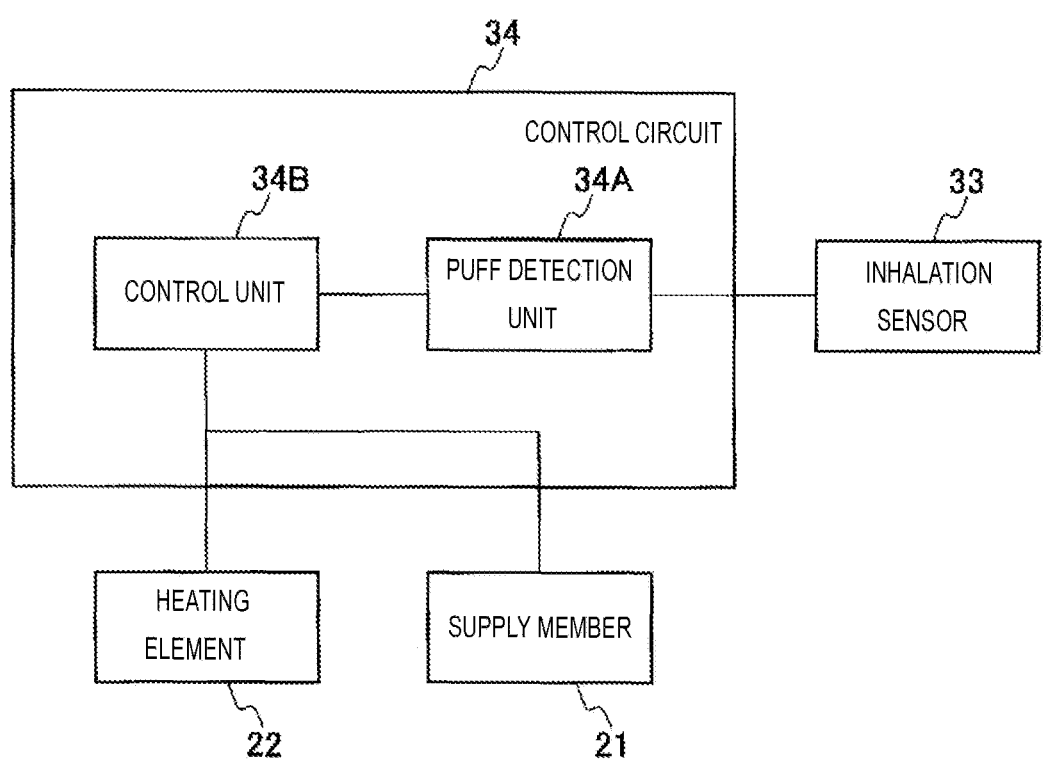
FIG. 2 is a diagram illustrating a control circuit 34 according to the embodiment.

Hereinafter, the control circuit according to the embodiment will be described. FIG. 2 is a diagram illustrating the control circuit 34 according to the embodiment. The control circuit 34 has a puff detection unit 34A, and a control unit 34B.

The puff detection unit 34A is connected to the inhalation sensor 33, and detects puff operation of a user on the basis of a value output from the inhalation sensor 33. More specifically, the puff detection unit 34A detects behavior of the puff operation. As described below, a detection result is used for determination of a supply start condition. The detection result may be used to determine a supply end condition.

The control unit 34B is connected to the supply member 21 and the heating element 22, and controls the supply member 21 and the heating element 22 on the basis of the detection result of the puff detection unit 34A.

First, in case that the supply start condition is satisfied, the control unit 34B controls the supply member 21 to start supply of the aerosol source. In case that the supply end condition is satisfied, the control unit 34B controls the supply member 21 to end the supply of the aerosol source.

Figure 3:
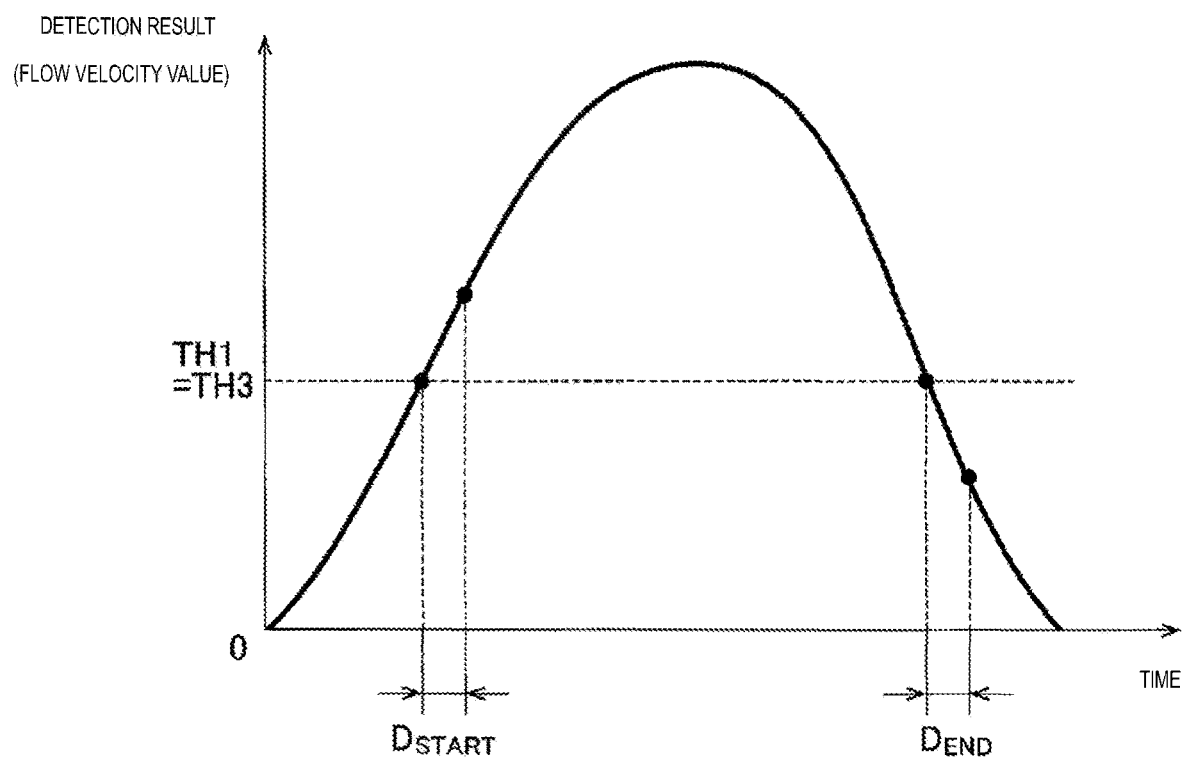
FIG. 3 is a diagram for illustrating supply of an aerosol source and heating of a heating element 22 according to the embodiment.

In the embodiment, whether or not the supply start condition and the supply end condition are satisfied is determined on the basis of a value output from the inhalation sensor 33, that is, the detection result of the puff detection unit 34A. Hereinafter, a case in which a physical parameter detected by the puff detection unit 34A is the flow velocity value will be described as an example. As illustrated in FIG. 3, the supply start condition is that the flow velocity value exceeds a threshold TH1, and the supply end condition is that the flow velocity value is below a threshold TH3. Although a case in which the threshold TH1 is the same as the threshold TH3 is illustrated in FIG. 3, the threshold TH1 and the threshold TH3 may be different from each other.

Of course, the physical parameter detected by the puff detection unit 34A may be a parameter other than the flow velocity value. Examples of the physical parameter include negative pressure value, and pressure value. As means for acquiring the physical parameter, a pressure sensor, a microphone sensor, or the like can be used. The pressure sensor, the microphone sensor, or the like may be implemented by only the inhalation sensor 33, or may be implemented by both the inhalation sensor 33 and the puff detection unit 34A. In such a case, necessary replacement is performed in accordance with the content of the physical parameter, so that whether or not the supply start condition and the supply end condition are satisfied can be of course determined.

Secondly, in case that a heating start condition is satisfied after the supply start condition is satisfied, the control unit 34B may start heating of the heating element 22. In case that a heating end condition is satisfied after the supply end condition is satisfied, the control unit 34B may end heating of the heating element 22.

In the embodiment, whether or not the heating start condition and the heating end condition are satisfied is determined on the basis of time that elapses after the supply start condition and the supply end condition are satisfied. As illustrated in FIG. 3, the heating start condition is that first predetermined time ($D_{START}$) elapses after the supply start condition is satisfied, and the heating end condition is that second predetermined time ($D_{END}$) elapses after the supply end condition is satisfied. The first predetermined time ($D_{START}$) is determined such that the sufficient aerosol source is supplied from the supply member 21 to the heating element 22. The second predetermined time ($D_{END}$) is determined such that a residue of the aerosol source in the heating element 22 or retention of the aerosol in the flow passage for the aerosol is suppressed. However, the first predetermined time ($D_{START}$) and the second predetermined time ($D_{END}$) may be the same, but may be different from each other. Additionally, the second predetermined time ($D_{END}$) may be zero.

The first predetermined time ($D_{START}$) or the second predetermined time ($D_{END}$) may be determined by supposing normal puff operation. The normal puff operation may be, not particularly limited, statistically determined on the basis of sampled data that is obtained by sampling a plurality of user's puff operations.

(Action and Effects)

In the embodiment, the heating element 22 itself has the porous structure, and therefore the heating element 22 can hold the aerosol source, any member for holding the aerosol source is not required, and the aerosol source can be efficiently atomized. Furthermore, the heating element 22 is disposed apart from the discharge port 21B, and therefore heat transfer from the aerosol source on the heating element 22 side to the aerosol source on the supply member 21 side is suppressed in a state in which the aerosol source is not supplied from the supply member 21 to the heating element 22.

In the embodiment, in case that the heating start condition is satisfied after the supply start condition is satisfied, the flavor inhaler 100 may start heating of the heating element 22. According to such a configuration, heating is started after the aerosol source is sufficiently held by the heating element 22, and therefore most of the heating element 22 can be used to atomize the aerosol source, and the temperature of the heating element 22 is unlikely to be non-uniform. Accordingly, the aerosol source can be efficiently atomized. Furthermore, overheating of the heating element 22 can be suppressed in a state in which the aerosol source is not held by the heating element 22.

In the embodiment, in case that the heating end condition is satisfied after the supply end condition is satisfied, the flavor inhaler 100 may end heating of the heating element 22. According to such a configuration, it is possible to suppress the residue of the aerosol source in the heating element 22 in a stage of end of heating, and it is possible to suppress the retention of the aerosol in the flow passage for the aerosol in the stage of end of the puff operation.

As described above, start and end of the heating of the heating element 22 are controlled, so that electric power consumption can be suppressed compared to a conventional flavor inhaler. In the conventional flavor inhaler, a configuration in which the aerosol source is supplied in a state in which the heating element is being heated is employed, and therefore it should be noted that the electric power consumption of the conventional flavor inhaler is larger than the electric power consumption of the flavor inhaler 100 according to the embodiment. It should be noted that in a flavor inhaler having a wick to which an aerosol source is always supplied, control for start and end of the supply of the aerosol source does not exist, and is not an object to be compared with the flavor inhaler 100 according to the embodiment.

In the embodiment, the absorbing component 12 that absorbs aerosol which flocculates on the wall surface of the flow passage (a part of the air flow passage) of aerosol generated by the atomizing unit 20 is provided. According to such a configuration, according to such a configuration, deterioration of a member (for example, the flow passage member 13 or the flow passage member 23) due to flocculation of aerosol is suppressed.

[Modification 1]

Hereinafter, Modification 1 of the embodiment will be described. Hereinafter, points different from the embodiment will be mainly described.

In the embodiment, whether or not the heating start condition and the heating end condition are satisfied is determined on the basis of time that elapses after the supply start condition and the supply end condition are satisfied.

On the other hand, In Modification 1, whether or not a heating start condition and a heating end condition are satisfied is determined on the basis of a value output from an inhalation sensor 33, that is, a detection result of a puff detection unit 34A.

Figure 4:
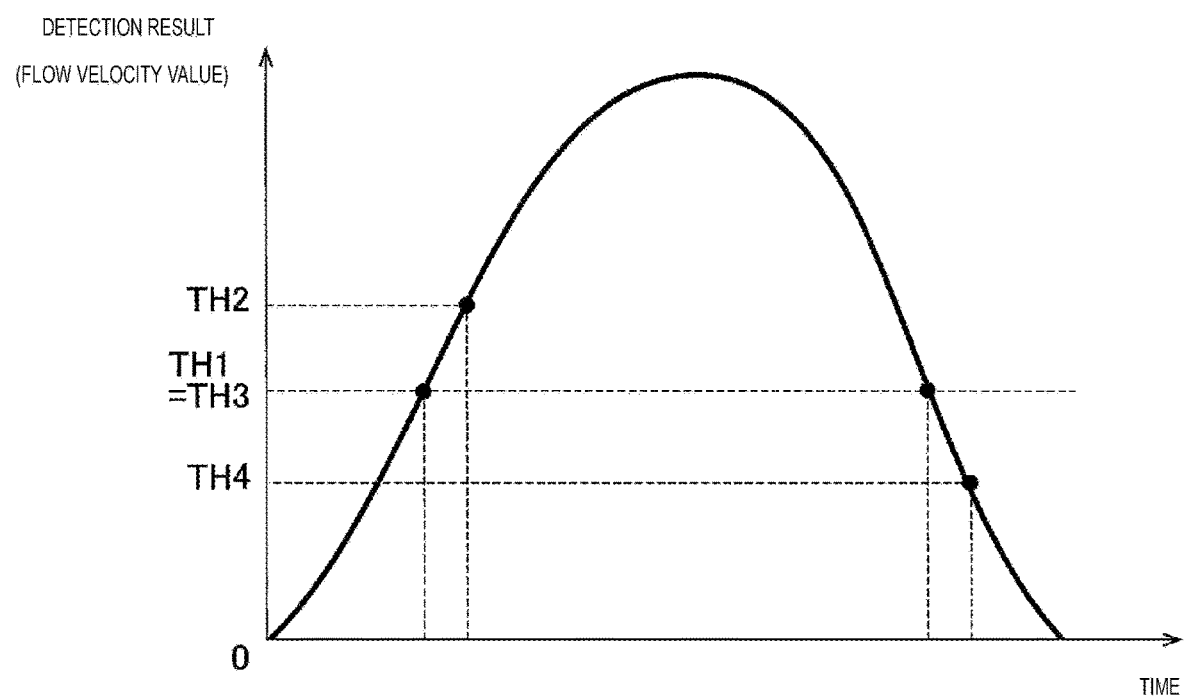
FIG. 4 is a diagram for illustrating supply of an aerosol source and heating of a heating element 22 according to Modification 1.

For example, a case in which the detection result is a flow velocity value will be described as an example. As illustrated in FIG. 4, the heating start condition is that the flow velocity value exceeds a threshold TH2 larger than a threshold TH1, and the heating end condition is that the flow velocity value is below a threshold TH4 smaller than a threshold TH3. The threshold TH2 is determined such that a sufficient aerosol source is supplied from a supply member 21 to a heating element 22. The threshold TH4 is determined such that a residue of the aerosol source in the heating element 22 or retention of aerosol in a flow passage for the aerosol is suppressed. However, the threshold TH4 may be the same as the threshold TH3.

Of course, the detection result may be a physical parameter other than the flow velocity value. In such a case, necessary replacement is performed in accordance with the content of the detection result, so that whether or not the heating start condition and the heating end condition are satisfied can be of course determined.

(Actions and Effects)

In Modification 1, whether or not the heating start condition and the heating end condition are satisfied is determined on the basis of the value output from the inhalation sensor 33. According to such a configuration, heating is performed in accordance with behavior of puff operation of a user, and therefore supply control and heating control can be suitably synchronized.

[Modification 2]

Hereinafter, Modification 2 of the embodiment will be described. Hereinafter, points different from Modification 1 will be mainly described.

Figure 5:
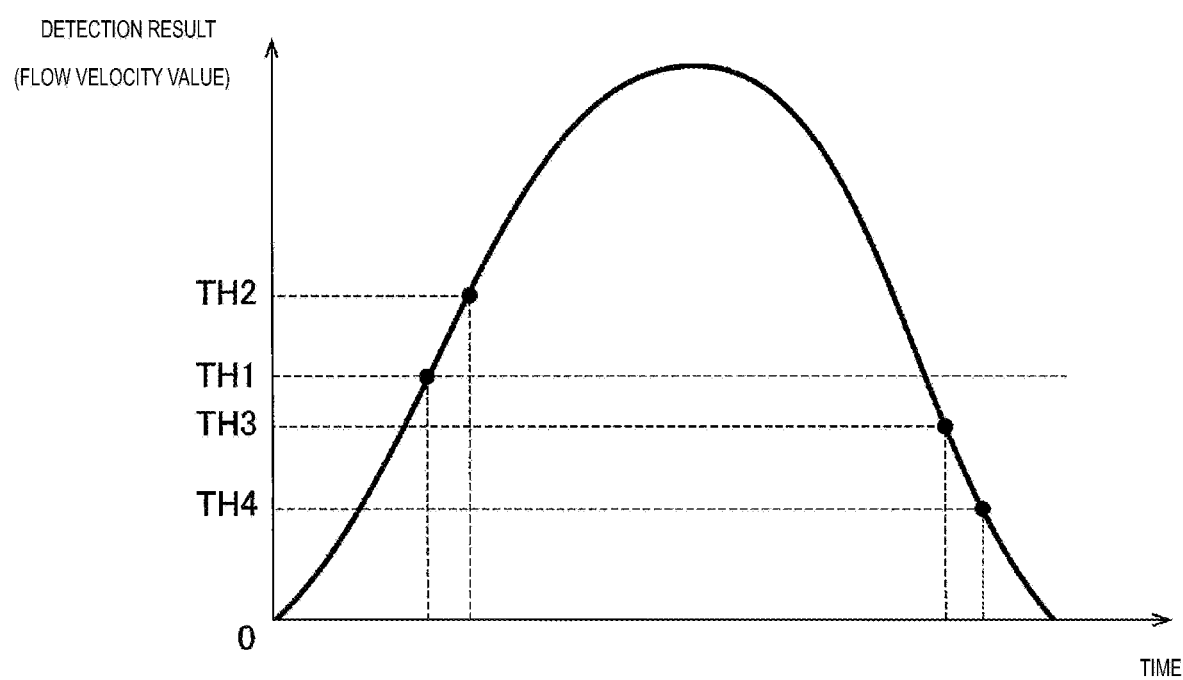
FIG. 5 is a diagram for illustrating supply of an aerosol source and heating of a heating element 22 according to Modification 2.
Figure 6:
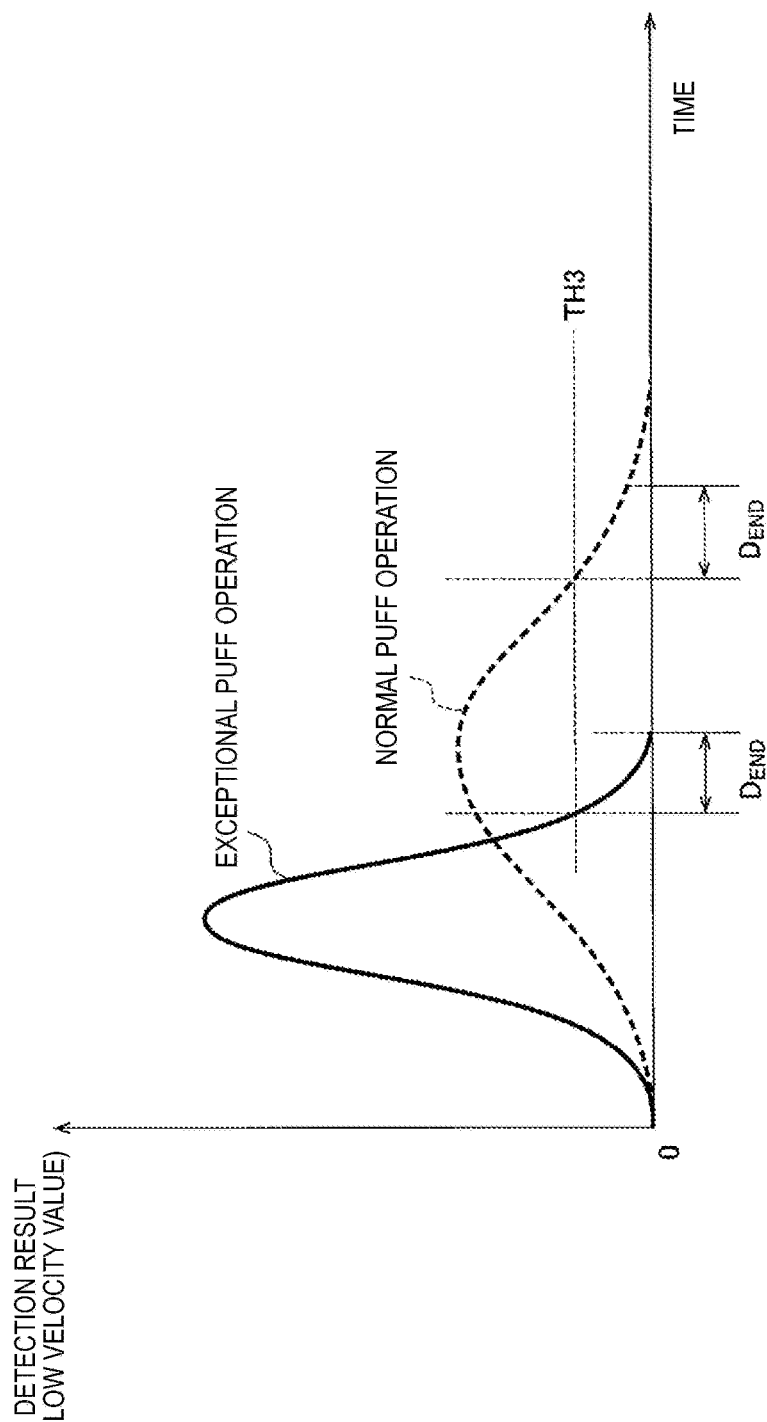
FIG. 6 is a diagram for illustrating supply of an aerosol source and heating of a heating element 22 according to Modification 3.
Figure 7:
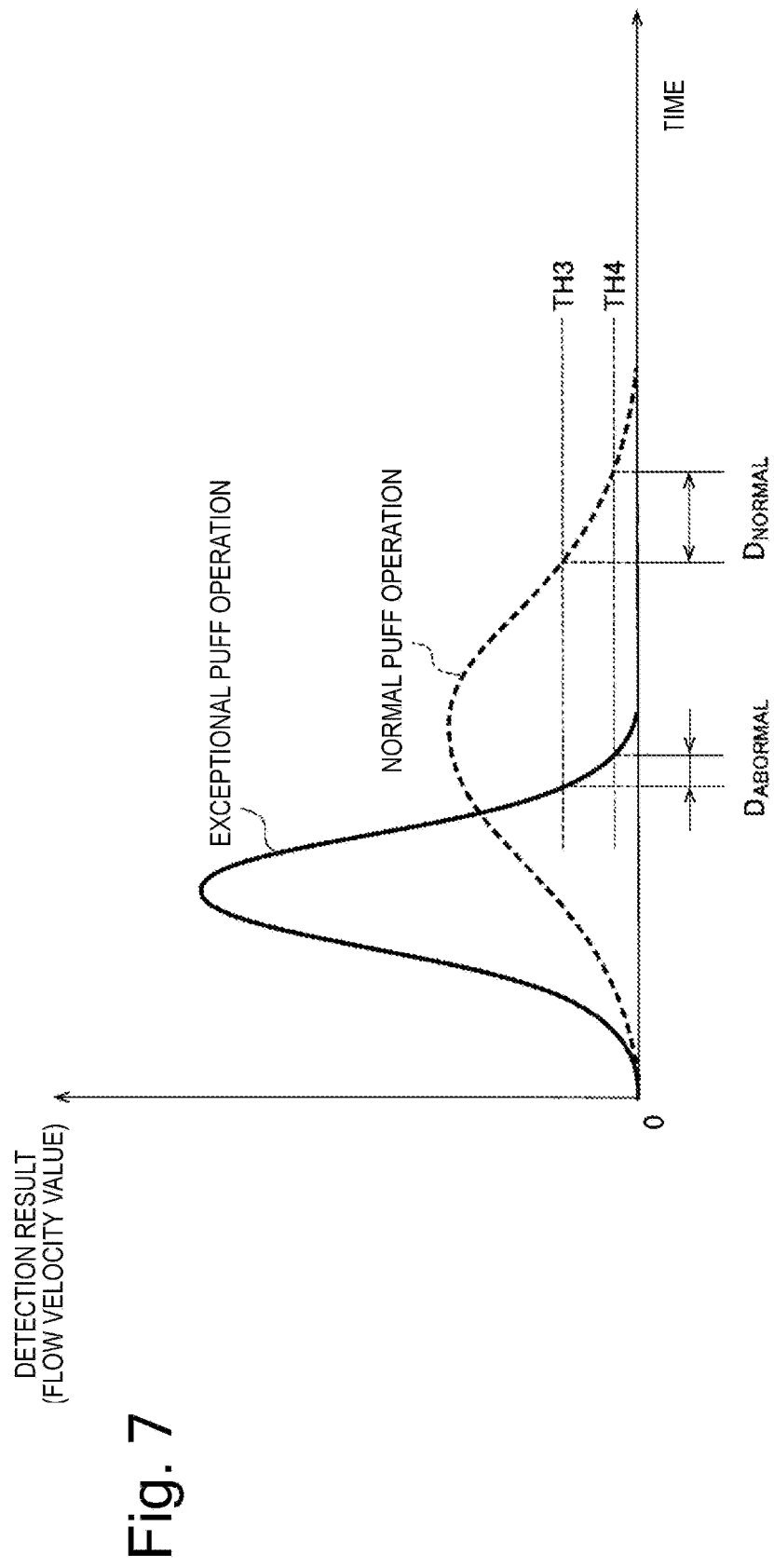
FIG. 7 is a diagram for illustrating supply of an aerosol source and heating of a heating element 22 according to Modification 4.

In Modification 1, the threshold TH1 used to determine the supply start condition is the same as the threshold TH3 used to determine the supply end condition. On the other hand, in Modification 2, a threshold TH1 used to determine a supply start condition is different from a threshold TH3 used to determine a supply end condition. For example, as illustrated in FIG. 5, the threshold TH3 used to determine the supply end condition may be a value smaller than the threshold TH1 used to determine the supply start condition.

(Actions and Effects)

In Modification 2, the threshold TH3 used to determine the supply end condition may be the value smaller than the threshold TH1 used to determine the supply start condition. According to such a configuration, while malfunction of supply start of an aerosol source is suppressed, time of supplying aerosol to the heating element 22 can be extended, and a degree of satisfaction of a user is improved.

[Modification 3]

Hereinafter, Modification 3 of the embodiment will be described. Hereinafter, points different from the embodiment will be mainly described.

Although not particularly described in the embodiment, exceptional puff operation will be described in Modification 3. The exceptional puff operation is puff operation performed for shorter time than normal puff operation referred to when the above second predetermined time ($D_{END}$) is determined.

In the exceptional puff operation, in a stage of ending heating of a heating element 11, a possibility that puff operation by a user is already ended is considered. In such a case, there is a possibility that retention of aerosol in the flow passage for the aerosol is generated in the stage of ending puff operation.

Accordingly, in Modification 3, in case that end of the puff operation by the user is detected from when the supply end condition is satisfied until when the second predetermined time ($D_{END}$) elapses, the control unit 34B ends heating of the heating element 22 before the second predetermined time ($D_{END}$) elapses. The control unit 34B may end the heating of the heating element 22 at the timing of detecting the end of the puff operation of the user. According to such a configuration, it is possible to suppress the retention of the aerosol in the flow passage for the aerosol in a stage of ending the puff operation.

However, when the above control is performed, there is a possibility of generating the residue of the aerosol source in the heating element 22 in a stage of ending heating.

Accordingly, in Modification 3, in case that heating of the heating element 22 is ended before the second predetermined time ($D_{END}$) elapses in n (n is an integer of one or more)-th puff operation, when more relaxed condition than the heating start condition is satisfied in (n+1)-th puff operation, the control unit 34B starts heating of the heating element 22. For example, the more relaxed condition than the relaxation of the heating start condition may be that time shorter than first predetermined time ($D_{START}$) elapses after the supply start condition is satisfied. The more relaxed condition than the relaxation of the heating start condition may be the same as the supply start condition, and may be a condition satisfied before the supply start condition is satisfied. According to such a configuration, an aerosol source that remains in the heating element 22 in n-th puff operation can be suitably atomized in an initial stage of (n+1)-th puff operation.

Alternatively, in Modification 3, in case that heating of the heating element 22 is ended before the second predetermined time ($D_{END}$) elapses in n (n is an integer of one or more)-th puff operation, the control unit 34B may control atomization of the aerosol source by the heating element 22 such that electric power larger than electric power supplied to the heating element 22 in n-th puff operation is supplied to the heating element 22 in (n+1)-th puff operation. For example, the control unit 34B may control such that electric power larger than electric power supplied to the heating element 22 in n-th puff operation is supplied to the heating element 22 over whole of (n+1)-th puff operation. Alternatively, the control unit 34B may control such that electric power larger than electric power supplied to the heating element 22 in n-th puff operation is supplied to the heating element 22 in only the first half of (n+1)-th puff operation. According to such a configuration, an aerosol source that remains in the heating element 22 in n-th puff operation can be suitably atomized in (n+1)-th puff operation.

Alternatively, in Modification 3, the control unit 34B may control atomization of the aerosol source by the heating element 22 such that electric power larger than electric power supplied before the supply end condition is satisfied is supplied to the heating element 22 from when the supply end condition is satisfied until when the heating end condition is satisfied. Consequently, the length of the second predetermined time ($D_{END}$) can be set shorter.

It should be noted that the retention (flocculation) of the aerosol in the flow passage for the aerosol can be suppressed by the above absorbing component 12.

[Modification 4]

Hereinafter, Modification 4 of the embodiment will be described. Hereinafter, points different from Modification 1 or Modification 2 will be mainly described.

Although not particularly described in Modification 1 or Modification 2, exceptional puff operation will be described in Modification 4. The exceptional puff operation is puff operation performed for shorter time than normal puff operation referred to when the above threshold TH4 is determined.

Time from end of supply of the aerosol source to end of heating in the exceptional puff operation ($D_{ABNORMAL}$) is shorter than time from end of supply of the aerosol source to end of heating in the normal puff operation ($D_{NORMAL}$). Accordingly, in a stage of end of heating, there is a possibility that a residue of the aerosol source in a heating element 22 is generated.

Accordingly, in Modification 4, in case that time from when a supply end condition is satisfied until when a heating end condition is satisfied ($D_{ABNORMAL}$) is shorter than predetermined time (for example, time equal to or less than a lower limit of an obtainable value of time ($D_{NORMAL}$) in the normal puff operation) in n (n is an integer of one or more)-th puff operation, when a more relaxed condition than the heating start condition is satisfied in (n+1)-th puff operation, the control unit starts heating of the heating element. For example, the more relaxed condition than relaxation of the heating start condition may be that a flow velocity value exceeds a threshold TH2' smaller than a threshold TH2. The more relaxed condition than the relaxation of the heating start condition may be the same as the supply start condition, and may be a condition satisfied before the supply start condition is satisfied. In such a case, the threshold TH2' may be the same as a threshold TH1, or may be a value smaller than the threshold TH1. According to such a configuration, an aerosol source that remains in the heating element 22 in n-th puff operation can be suitably atomized in an initial stage of (n+1)-th puff operation.

Alternatively, in Modification 4, in case that time from when the supply end condition is satisfied until when the heating end condition is satisfied ($D_{ABNORMAL}$) is shorter than predetermined time (for example, time equal to or less than a lower limit of an obtainable value of time ($D_{NORMAL}$) in the normal puff operation) in n (n is an integer of one or more)-th puff operation, the control unit may control atomization of the aerosol source by the heating element 22 such that electric power larger than electric power supplied to the heating element 22 in the n-th puff operation is supplied to the heating element 22 in (n+1)-th puff operation. For example, the control unit 34B may control such that electric power larger than electric power supplied to the heating element 22 in n-th puff operation is supplied to the heating element 22 over whole of (n+1)-th puff operation. Alternatively, the control unit 34B may control such that electric power larger than electric power supplied to the heating element 22 in n-th puff operation is supplied to the heating element 22 in only the first half of (n+1)-th puff operation. According to such a configuration, an aerosol source that remains in the heating element 22 in n-th puff operation can be suitably atomized in (n+1)-th puff operation.

[Modification 5]

Hereinafter, Modification 5 of the embodiment will be described. Hereinafter, points different from the embodiment will be mainly described.

In the embodiment, the supply member 21 is a member that supplies an aerosol source by a droplet supply method similar to a method used in an ink jet printer. However, the embodiment is not limited to this.

Figure 8:
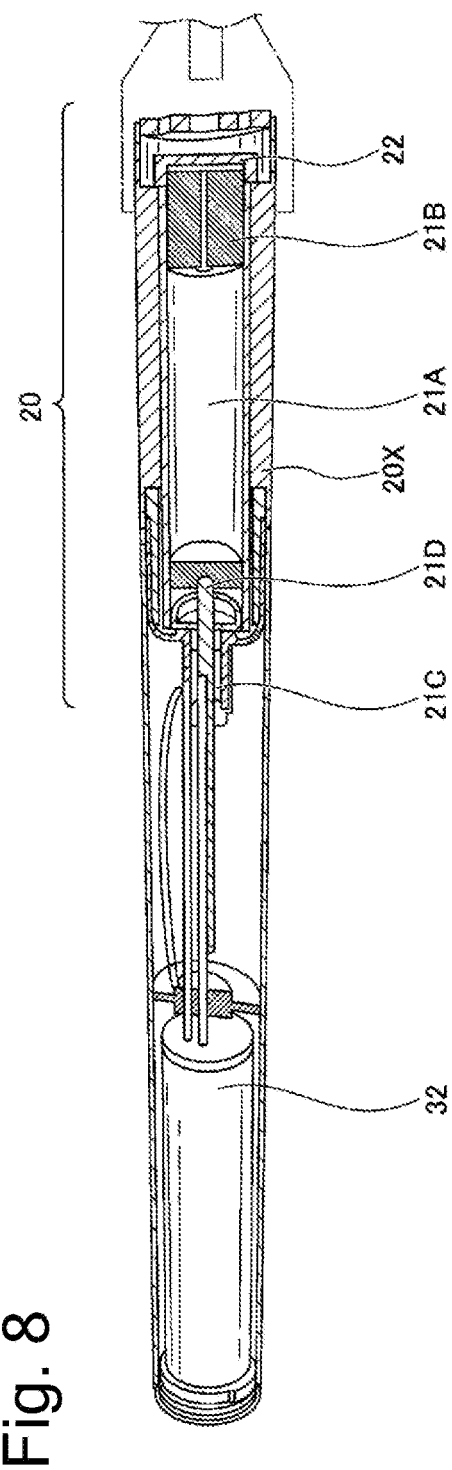
FIG. 8 is a diagram illustrating a supply member 21 according to Modification 5.

More specifically, the supply member 21 may include discharging means as a member different from the discharge port 21B. The discharging means may be means for supplying an aerosol source by a piston method. For example, as illustrated in FIG. 8, the supply member 21 has an actuator 21C and a piston 21D in addition to a storage part 21A and a discharge port 21B. The actuator 21C performs reciprocating motion of the piston 21D by transmitting power to a connecting rod. Consequently, an aerosol source is supplied from the discharge port 21B to a heating element 22.

Figure 9:
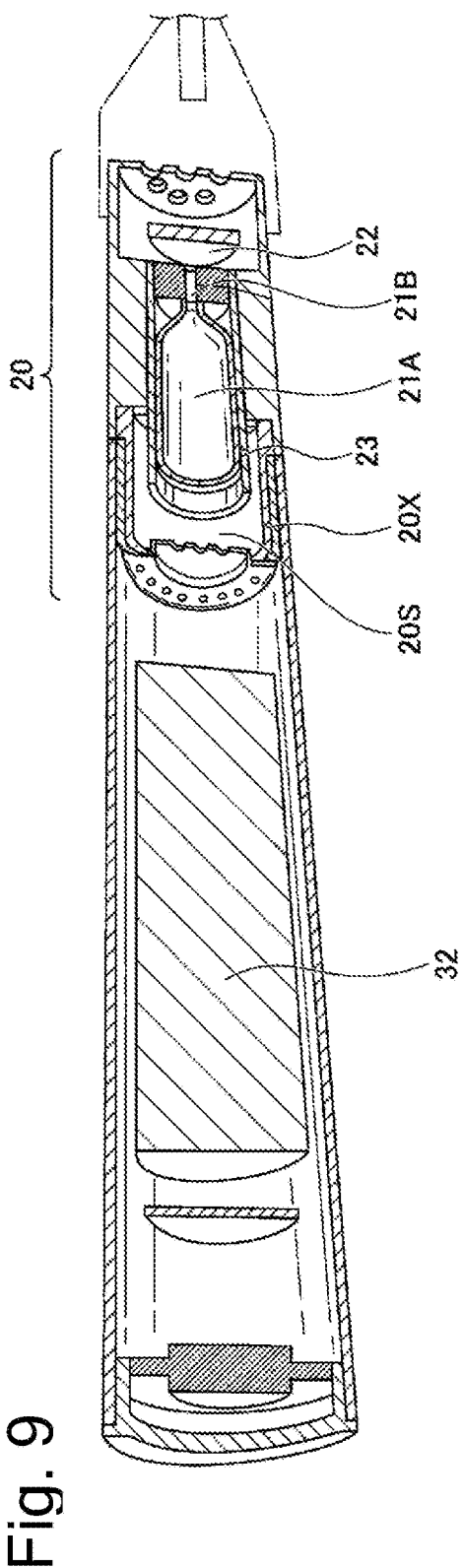
FIG. 9 is a diagram illustrating the supply member 21 according to Modification 5.

Alternatively, as another example in which the supply member 21 includes discharging means as a member different from the discharge port 21B, the discharging means may be means for supplying an aerosol source by differential pressure in an air flow passage. For example, as illustrated in FIG. 9, a supply member 21 has a storage part 21A and a discharge port 21B, and the storage part 21A is composed of a flexible bag. Differential pressure in an air flow passage 21S is changed by puff operation of a user, and stress is applied to the flexible bag by change of the differential pressure in the air flow passage 21S. Consequently, the aerosol source is supplied from the discharge port 21B to a heating element 22.

In case that the supply member 21 has a configuration illustrated in FIG. 9, an aerosol source is supplied by differential pressure generated by puff operation as a trigger, and therefore it should be noted that control of a control circuit 34 is unnecessary in supply of the aerosol source.

[Modification 6]

Hereinafter, Modification 6 of the embodiment will be described. Hereinafter, points different from Modifications 1, 2 will be mainly described.

In the embodiment, Modifications 1, 2, the flavor inhaler 100 has the inhalation sensor 33. The inhalation sensor 33 is used to determine whether or not the supply start condition and the supply end condition are satisfied. Alternatively, the inhalation sensor 33 is used to determine whether or not the heating start condition and the heating end condition are satisfied.

Figure 10:
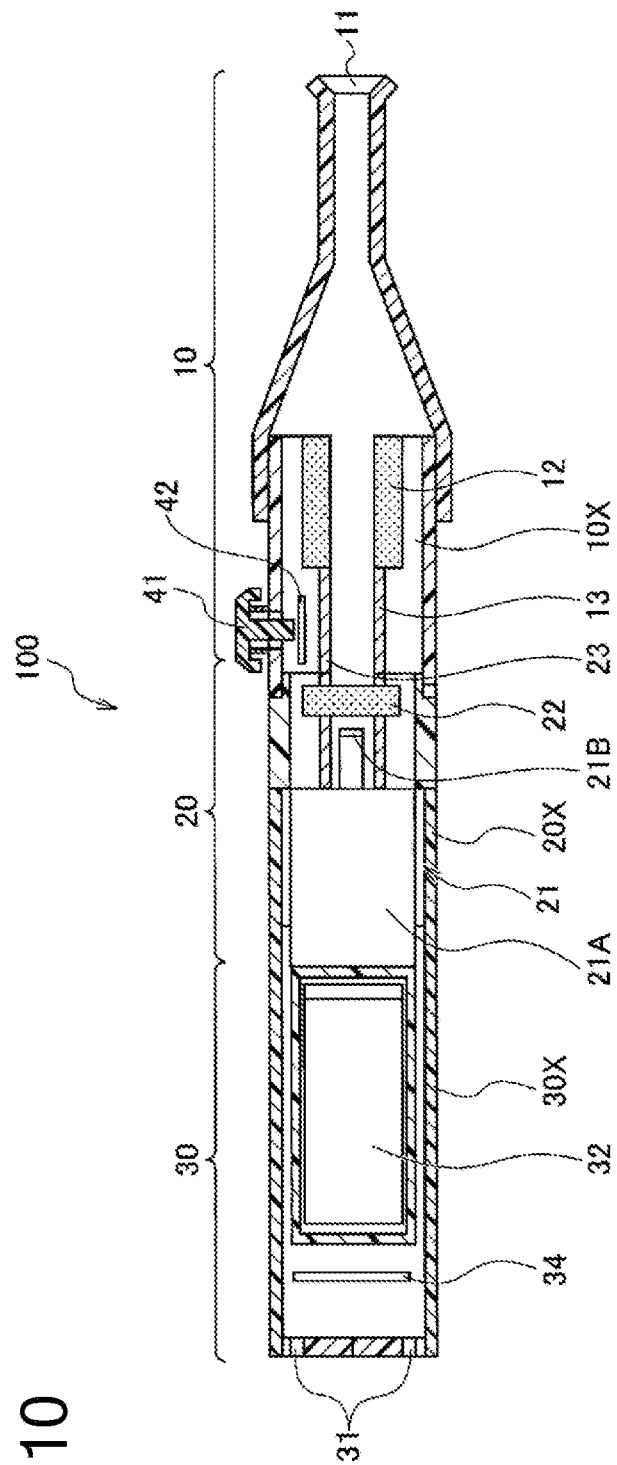
FIG. 10 is a diagram illustrating a flavor inhaler 100 according to Modification 6.

On the other hand, in Modification 6, as illustrated in FIG. 10, a flavor inhaler 100 has a push button 41 and a pushing down sensor 42. The push button 41 is a user interface manipulated by a user. The push button 41 may be provided on a side surface of the flavor inhaler 100. The push button 41 may be provided in a tip (non-mouthpiece end) of the flavor inhaler 100. The pushing down sensor 42 is a sensor that detects pushing down of the push button 41. The pushing down sensor 42 is an example of a detection sensor that detects predetermined manipulation of a user.

A detection result of the pushing down sensor 42 may be used to determine whether or not a supply start condition and a supply end condition are satisfied. The detection result of the pushing down sensor 42 may be used to determine whether or not a heating start condition and a heating end condition are satisfied.

For example, the supply start condition or the heating start condition may be that the pushing down sensor 42 detects a state in which the push button 41 is pushed down. The supply end condition or the heating end condition may be that the pushing down sensor 42 detects a state in which the push button 41 is not pushed down. The supply start condition or the heating start condition may be that the pushing down sensor 42 detects pushing down of the push button 41 in a state in which supply or heating is not performed. The supply end condition or the heating end condition may be that the pushing down sensor 42 detects pushing down of the push button 41 in a state in which supply or heating is performed.

Figure 11:
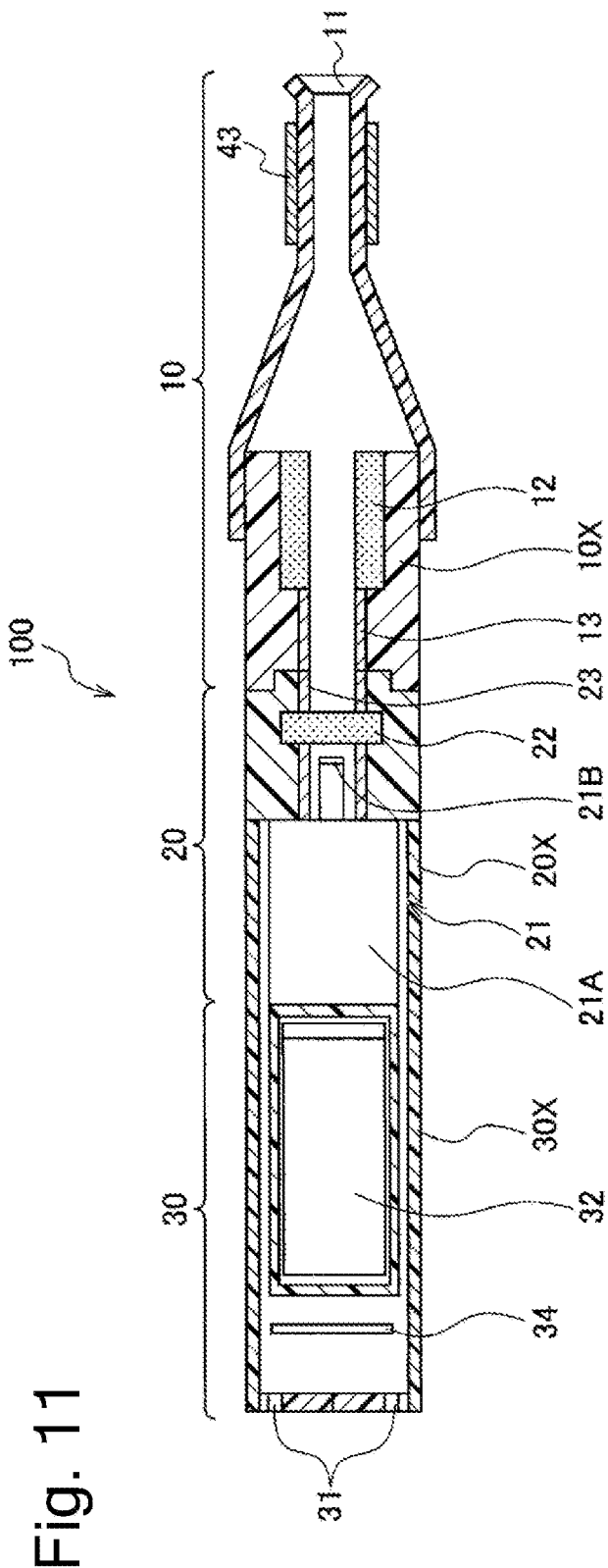
FIG. 11 is a diagram illustrating the flavor inhaler 100 according to Modification 6.

Alternatively, in Modification 6, as illustrated in FIG. 11, a flavor inhaler 100 has a push button 41 and a lip sensor 43. The lip sensor 43 is a sensor that detects contact of a lip of a user with a mouthpiece unit 10. The lip sensor 43 is an example of a detection sensor that detects predetermined manipulation of a user.

A detection result of the lip sensor 43 may be used to determine whether or not a supply start condition and a supply end condition are satisfied. The detection result of the lip sensor 43 may be used to determine whether or not a heating start condition and a heating end condition are satisfied.

For example, the supply start condition or the heating start condition may be that the lip sensor 43 detects a contact state with a lip. The supply end condition or the heating end condition may be that the lip sensor 43 detects a non-contact state with a lip.

In Modification 6, the "manipulation" is different from the above "puff operation". The "manipulation" is that which does not directly involve inhalation of aerosol, for example, contact, pushing down, or the like.

[Modification 7]

Hereinafter, Modification 7 of the embodiment will be described. Hereinafter, points different from the embodiment will be mainly described.

In Embodiment 7, in case that the heating start condition is satisfied after the supply start condition is satisfied, the control unit 34B starts heating of the heating element 22.

On the other hand, in Modification 7, a control unit 34B may start heating of a heating element 22 before a supply start condition is satisfied. More specifically, the control unit 34B controls atomization of an aerosol source such that the temperature of the heating element 22 is less than a boiling point of an aerosol source until the supply start condition is satisfied. The control unit 34B controls atomization of the aerosol source such that the temperature of the heating element 22 is not less than the boiling point of the aerosol source after the supply start condition is satisfied.

Figure 12:
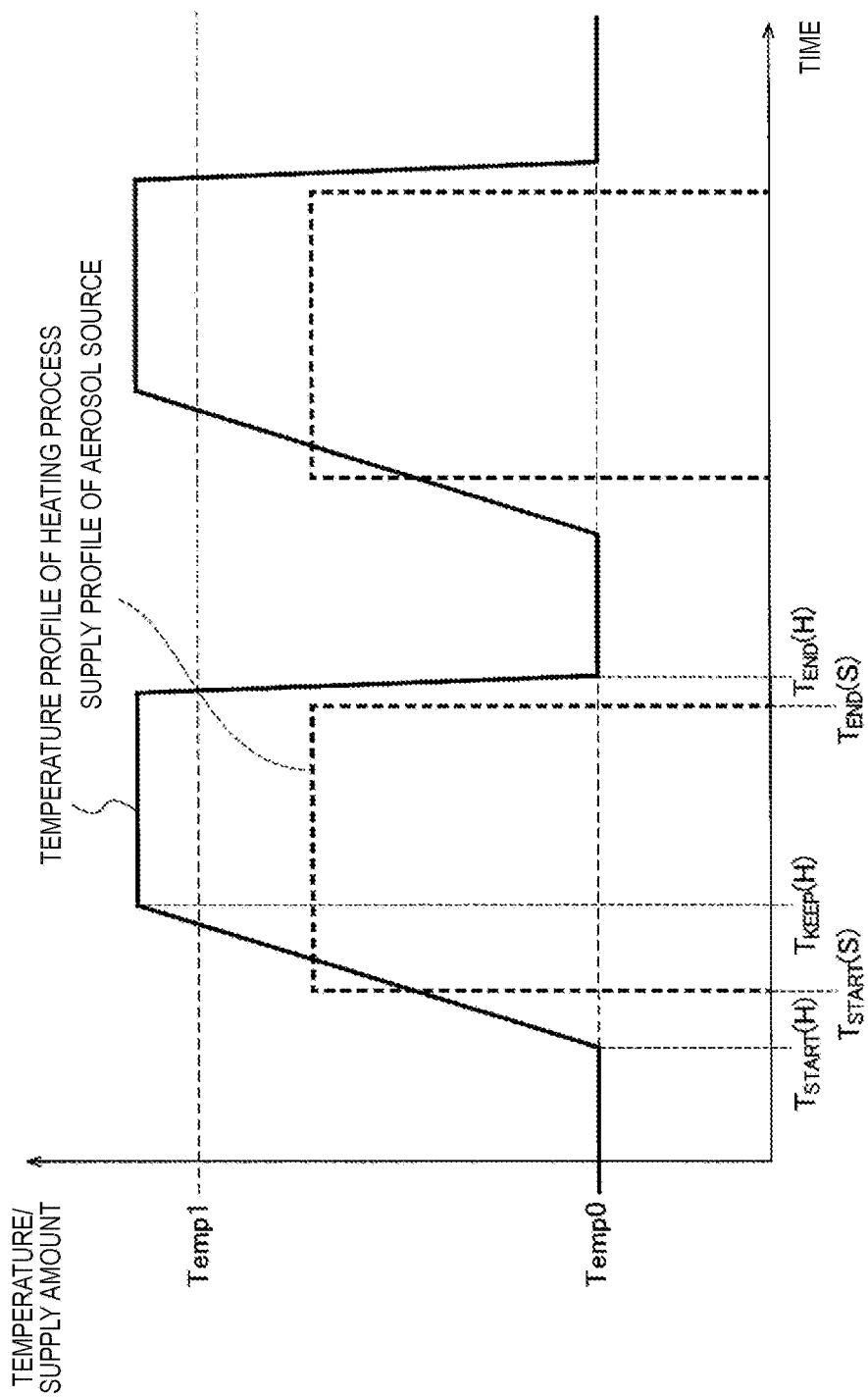
FIG. 12 is a diagram for illustrating supply of an aerosol source and heating of a heating element 22 according to Modification 7.

For example, as illustrated in FIG. 12, a case in which supply of the aerosol source is started at time $T^{START}(S)$, and the supply of the aerosol source is ended at end $T_{END}(S)$ is considered. In such a case, heating of the heating element 22 is started at the time $T_{START}(H)$, and the heating of the heating element 22 is ended at the time $T_{END}(H)$.

In such a case, the temperature of the heating element 22 is a temperature Temp0 (normal temperature) before the time $T_{START}(H)$, the temperature of the heating element 22 rises after the time $T_{START}(H)$, the temperature of the heating element 22 reaches a temperature higher than a temperature Temp1 (boiling point) at time $T_{KEEP}(H)$, and the temperature of the heating element 22 returns to the temperature Temp0 (normal temperature) at the time $T_{END}(H)$. Thus, the temperature of the heating element 22 is controlled to a temperature below the temperature Temp1 (boiling point) before the time $T_{START}(S)$, and is controlled to a temperature not less than the temperature Temp1 (boiling point) after the time $T_{START}(S)$. The temperature of the heating element 22 may be replaced with the temperature of the aerosol source held by the heating element 22.

Other Embodiment

Although the present invention has been described with the above embodiment, it is not to be understood that descriptions and drawings that constitute part of the present disclosure are intended to limit the invention. This disclosure will reveal various alternative embodiments, examples, and applications to those skilled in the art.

In the embodiment, both of whether or not the heating start condition is satisfied and whether or not the heating end condition is satisfied are determined on the basis of time that elapses after the supply start condition and the supply end condition are satisfied. However, the embodiment is not limited to this. Either of whether or not the heating start condition is satisfied or whether or not the heating end condition is satisfied may be determined on the basis of the time that elapses after the supply start condition and the supply end condition are satisfied.

In Modification 1, both whether or not the heating start condition and the heating end condition are satisfied are determined on the basis of the value output from the inhalation sensor 33, that is, the detection result of the puff detection unit 34A. However, Modification 1 is not limited to this. Either whether or not the heating start condition and the heating end condition are satisfied may be determined on the basis of the value output from the inhalation sensor 33, that is, the detection result of the puff detection unit 34A.

The embodiment, Modifications 1 to 7 may be combined with each other. The flavor inhaler 100 may have 2 or more sensors among the inhalation sensor 33 (FIG. 1), the pushing down sensor 42 (FIG. 10) and the lip sensor 43 (FIG. 11). Whether or not each condition (the supply start condition, the supply end condition, the heating start condition, and the heating end condition) is satisfied may be determined by using the arbitrary two or more sensors.

For example, whether or not the supply start condition and the supply end condition (hereinafter, supply conditions) are satisfied may not be determined like a case in which means for supplying the aerosol source by differential pressure in the air flow passage is used as the supply member 21 (for example, a case in which the flexible bag illustrated in FIG. 9 is used). However, even the case in which the flexible bag illustrated in FIG. 9 is used, the control circuit 34 may be able to detect the supply start or the supply end of the aerosol source. That is, the control circuit 34 may detect that the supply start condition is satisfied, by detection of the supply start of the aerosol source, and may detect that the supply end condition is satisfied by detection of the supply end of the aerosol source. Whether or not the supply conditions are satisfied may be determined by using the inhalation sensor 33 (FIG. 1), may be determined by using the pushing down sensor 42 (FIG. 10), or may be determined by using the lip sensor 43 (FIG. 11).

Alternatively, whether or not the heating start condition and the heating end condition (hereinafter, heating conditions) are satisfied may be determined by the elapsed time, as illustrated in FIG. 3. Whether or not the heating conditions are satisfied may be determined by using the inhalation sensor 33 (FIG. 1), may be determined by using the pushing down sensor 42 (FIG. 10), or may be determined by using the lip sensor 43 (FIG. 11).

As described above, combination of the sensors that determine whether or not each condition is satisfied is not particularly limited, and may be various combination.

For example, in case that the flexible bag illustrated in FIG. 9 is used, whether or not the heating condition is satisfied may be determined by using the inhalation sensor 33 (FIG. 1), the elapsed time (FIG. 3), or the pushing down sensor 42 (FIG. 10). Alternatively, whether or not the supply conditions are satisfied may be determined by using the pushing down sensor 42 (FIG. 10), and whether or not the heating condition are satisfied may be determined by using the inhalation sensor 33 (FIG. 1), the elapsed time (FIG. 3), or the lip sensor 43 (FIG. 11). Alternatively, whether or not the supply conditions are satisfied may be determined by using the lip sensor 43 (FIG. 11), and whether or not the heating conditions are satisfied may be determined by using the inhalation sensor 33 (FIG. 1), the elapsed time (FIG. 3), or the pushing down sensor 42 (FIG. 10). Combination of these sensors are an example, and other combination may be of course employed.

Although not particularly described in the embodiment, electric power may be controlled by a duty ratio, or may be controlled by a voltage value to be applied to the heating element 22.

INDUSTRIAL APPLICABILITY

According to the embodiment, a member for holding an aerosol source does not need to be separately provided, and it is possible to provide a flavor inhaler and an atomizing unit enabling efficient atomization of an aerosol source.

The invention claimed is:

1. A flavor inhaler comprising:
a heating element that atomizes an aerosol source;
a supply member that has a discharge port for supplying the aerosol source to the heating element; and
a control unit that controls atomization of the aerosol source by the heating element, wherein
the heating element has a porous structure, and is disposed apart from the discharge port,
in case that a supply start condition is satisfied, supply of the aerosol source is started, and
in case that a heating start condition is satisfied after the supply start condition is satisfied, the control unit starts heating of the heating element,
in case that a supply end condition is satisfied, supply of the aerosol source is ended, in case that a heating end condition is satisfied after the supply end condition is satisfied, the control unit ends heating of the heating element, and
in case that time from when the supply end condition is satisfied until when the heating end condition is satisfied is shorter than predetermined time in n (n is an integer of one or more)-th puff operation and in case that a condition that can be satisfied more easily than the heating start condition is satisfied in (n+1)-th puff operation, the control unit starts heating of the heating element in the (n+1)-th puff operation.

2. The flavor inhaler according to claim 1, wherein the heating element is a heating resistor composing the porous structure.

3. The flavor inhaler according claim 1, wherein
the heating start condition is that first predetermined time elapses after the supply start condition is satisfied.

4. The flavor inhaler according to claim 1, comprising
an inhalation sensor that detects puff operation of a user, wherein
the heating start condition is determined on the basis of a value output from the inhalation sensor.

5. The flavor inhaler according to claim 1, comprising
a detection sensor that detects first predetermined manipulation of a user, wherein
the heating start condition is to detect the first predetermined manipulation.

6. The flavor inhaler according to claim 1, comprising:
an inhalation sensor that detects puff operation of a user, wherein
the heating end condition is determined on the basis of a value output from the inhalation sensor.

7. The flavor inhaler according to claim 1, comprising:
a detection sensor that detects second predetermined manipulation of a user, wherein
the heating start condition is to detect the second predetermined manipulation.

8. The flavor inhaler according to claim 1, wherein
in case that a supply start condition is satisfied, supply of the aerosol source is started,
the control unit controls atomization of the aerosol source such that a temperature of the heating element becomes less than a boiling point of the aerosol source until the supply start condition is satisfied, and
the control unit controls atomization of the aerosol source such that a temperature of the heating element becomes not less than the boiling point of the aerosol source after the supply start condition is satisfied.

9. The flavor inhaler according to claim 1, wherein
an absorbing member that absorbs aerosol which flocculates on a wall surface of a flow passage is provided on the flow passage for the aerosol generated by atomization of the aerosol source.

10. The flavor inhaler according to claim 1 wherein
the control unit controls atomization of the aerosol source by the heating element such that electric power larger than electric power supplied before the supply end condition is satisfied is supplied to the heating element from when the supply end condition is satisfied until when the heating end condition is satisfied.

11. A flavor inhaler comprising:
a heating element that atomizes an aerosol source;
a supply member that has a discharge port for supplying the aerosol source to the heating element; and
a control unit that controls atomization of the aerosol source by the heating element, wherein
the heating element has a porous structure, and is disposed apart from the discharge port,
in case that a supply start condition is satisfied, supply of the aerosol source is started, in case that a heating start condition is satisfied after the supply start condition is satisfied, the control unit starts heating of the heating element,
in case that a supply end condition is satisfied, supply of the aerosol source is ended,
in case that a heating end condition is satisfied after the supply end condition is satisfied, the control unit ends heating of the heating element, and
in case that time from when the supply end condition is satisfied until when the heating end condition is satisfied is shorter than predetermined time in n (n is an integer of one or more)-th puff operation, the control unit controls atomization of the aerosol source by the heating element such that electric power larger than electric power supplied to the heating element in the n-th puff operation is supplied to the heating element in (n+1)-th puff operation.

12. A flavor inhaler comprising:
a heating element that atomizes an aerosol source;
a supply member that has a discharge port for supplying the aerosol source to the heating element; and
a control unit that controls atomization of the aerosol source by the heating element, wherein
the heating element has a porous structure, and is disposed apart from the discharge port,
in case that a supply start condition is satisfied, supply of the aerosol source is started, in case that a heating start condition is satisfied after the supply start condition is satisfied, the control unit starts heating of the heating element,
in case that a supply end condition is satisfied, supply of the aerosol source is ended,
in case that a heating end condition is satisfied after the supply end condition is satisfied, the control unit ends heating of the heating element, wherein the heating end condition is that second predetermined time elapses after the supply end condition is satisfied, and
in case that end of puff operation of the user is detected before the second predetermined time elapses after the supply end condition is satisfied, the control unit ends heating of the heating element before the second predetermined time elapses.

13. The flavor inhaler according to claim 12, wherein
in case that heating of the heating element is ended before the second predetermined time elapses in n (n is an integer of one or more)-th puff operation, when a more relaxed condition than the heating start condition is satisfied in (n+1)-th puff operation, the control unit starts heating of the heating element.

14. The flavor inhaler according to claim 12, wherein
in case that heating of the heating element is ended before the second predetermined time elapses inn (n is an integer of one or more)-th puff operation, the control unit controls atomization of the aerosol source by the heating element such that electric power larger than electric power supplied to the heating element in the n-th puff operation is supplied to the heating element in (n+1)-th puff operation.

* * * * *